US00PP16152P3

(12) United States Plant Patent
Bessho

(10) Patent No.: US PP16,152 P3
(45) Date of Patent: Dec. 13, 2005

(54) PORTULACA PLANT NAMED 'KAKEGAWA CY4'

(50) Latin Name: *Portulaca oleracea*
Varietal Denomination: Kakegawa CY4

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 10/058,403

(22) Filed: Jan. 30, 2002

(65) Prior Publication Data

US 2003/0145359 P1 Jul. 31, 2003

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—June Hwu
(74) *Attorney, Agent, or Firm*—Jondle & Associates P.C.

(57) ABSTRACT

Portulaca 'Kakegawa CY4' is a new variety of *Portulaca oleracea*. This plant has a vigorous, spreading plant growth which produces unique purple color with yellow edges on the flowers.

1 Drawing Sheet

Genus and species: *Portulaca oleracea*.
Variety denomination:
'Kakegawa CY4'.

BACKGROUND OF THE NEW PLANT

This invention relates to a new and distinct cultivar of Portulaca plant, hereinafter referred to by the name 'Kakegawa CY4'. Portulaca 'Kakegawa CY4' is a new variety of *Portulaca oleracea*. The plant has a vigorous spreading growth habit and can be used as a groundcover. It can also be used in a potted or hanging basket presentation. The invention's flowers are a unique purple color with yellow edges. The flowers are single and measure approximately 3.5 centimeters in diameter when fully open. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Kakegawa CY4' has been reproduced by stem cuttings in Salinas, Calif., and all of the characteristics thereof have been determined to be firmly fixed.

The new variety originated from a hybridization made in June, 1994 between the varieties 'Duet Yellow' (not patented) and 'Duet Rose' (not patented). $F_1$ seed was sown from this cross in January, 1995 and three plants were selected for having bi-color rose with yellow petals the following summer. Ten plants were vegetatively propagated from each selection. In September, 1995 one line was selected as the most stable and uniform.

BRIEF DESCRIPTION OF DRAWINGS

The accompanying drawings serve by color photographic means to illustrate the new plant variety, 'Kakegawa CY4'.

The colors are represented as true as possible using conventional photographic procedures.

DETAILED DESCRIPTION OF THE NEW VARIETY

Figure 2:
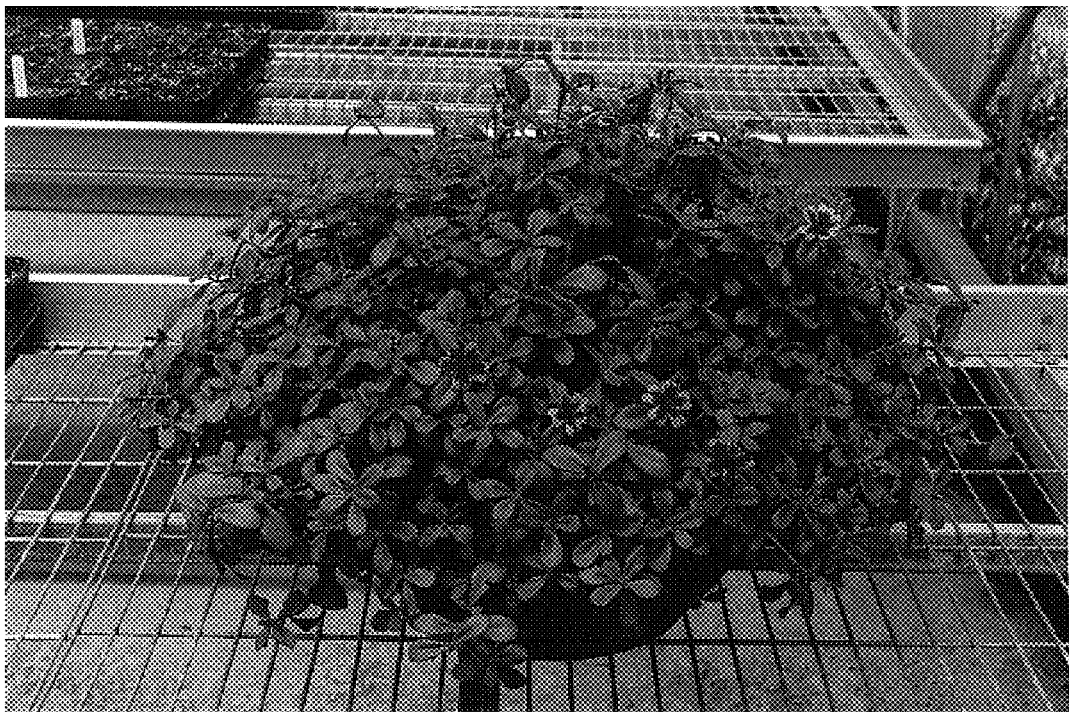
FIG. 2 is a view of several plants of the new cultivar growing in a 35.0 cm diameter pot.
Figure 1:
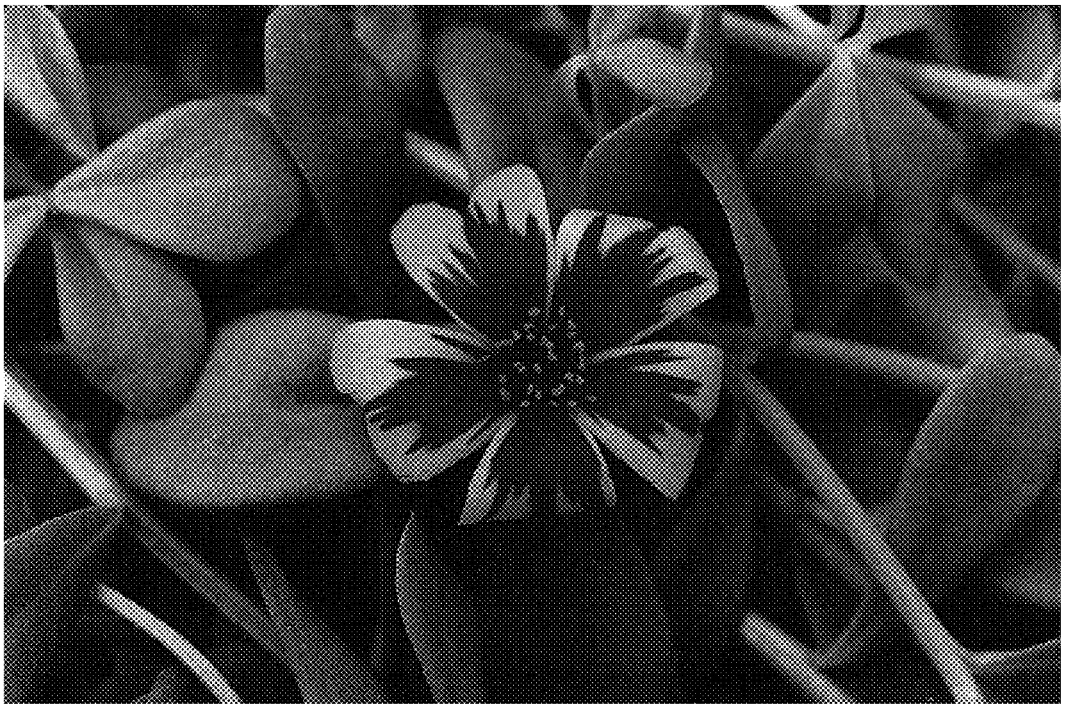
FIG. 1 is a close-up view of a 'Kakegawa CY4' flower illustrating its color and shape.

The following description is based on observations and measurements from 14–16 week old plants grown in 15 cm pots at Salinas, Calif. Plants were propagated from vegetative cuttings and grown in a glass greenhouse. These plants were grown in plastic pots containing a peat moss-based medium. Soluble fertilizer containing 18% nitrogen, 8% phosphorus and 18% potassium were applied every fourth irrigation. The plants were typically watered twice per week. Pots were topdressed with a slow release fertilizer containing 18% nitrogen, 8% phosphorus and 18% potassium. The average air temperature was 24° C.

Color designations were made according to The Royal Horticultural Society Colour Chart published by The Royal Horticultural Society of London, England.

Origin: Japan.
Parentage: Female parent — 'Duet Yellow' (not patented); Male parent — 'Duet Rose' (not patented).
Classification:
*Family.*—Portulacaceae.
*Genus.*—Portulaca.
*Species.*—*oleracea.*
*Commercial.*—Portulaca/purslane 'Kakegawa CY4'.
Plant:
*Growth habit.*—Prostrate.
*Plant height.*—23.0 cm.
*Spread.*—85 cm (in a six-inch pot).
*Life cycle.*—Perennial.
*Time to produce a rooted cutting.*—2 weeks.

*Time to bloom from propagation.*—6–8 weeks.

*Time to produce a rooted cutting.*—Vegetative cuttings root in 7–10 days after sticking into a rooting medium like a peat moss based mix; the cuttings will form roots without the use of overhead mist.

*Flowering season/requirements.*—Spring to Fall; flowers year round at temperatures of 24°–35° C.; day neutral light requirements.

*Temperature.*—Will not tolerate temperatures below 7° C.

Stem:

*Color.*—Yellowish green (144C).

*Anthocyanin.*—RHS 178B (greyed-red).

*Pubescence.*—Glabrous.

*Stem description.*—Round, slightly rough with lateral ridges.

*Diameter.*—5.0 mm.

*Length of internode.*—3.0–3.5 cm.

Leaf:

*Apex.*—Acute.

*Base.*—Cuneate.

*Arrangement.*—Alternate; leaves appear whorled towards the apex where internodes are not elongated.

*Leaf color.*—Upper surface RHS 137C (green); lower surface RHS 138C (green).

*Anthocyanin.*—RHS 178B (greyed-red).

*Margin.*—Entire.

*Length* (*average*).—3.0 cm.

*Width* (*average*).—1.5 cm.

*Shape.*—Obovate.

*Thickness.*—1.0 mm.

*Texture.*—Smooth.

*Petiole color.*—RHS N144D (yellow-green).

*Petiole length.*—2.0 mm.

*Petiole diameter.*—2.0–3.0 mm.

Flower:

*Calyx.*—2 sepals; 1.0 cm×8.0 mm; free.

*Sepal shape.*—Elliptic.

*Sepal texture.*—Smooth.

*Sepal margin.*—Entire, slightly sinuate.

*Sepal apex shape.*—Cuspidate.

*Corolla.*—5 petals; free.

*Flower diameter.*—3.0–3.5 cm.

*Bud color.*—RHS 138B (green).

*Bud shape.*—Round and pointed at the top.

*Bud surface.*—Shiny.

*Bud size.*—Length is 1.1–1.2 cm; diameter is 8 mm.

*Duration of flower life.*—One day.

*Flowering habit.*—Determinate.

*Placenta arrangement.*—Central.

*Inflorescence type.*—Solitary, sessile.

*Stamens.*—Filament color RHS 72A (red-purple) 6 mm in length; anther color RHS 9A (yellow) 1 mm in length.

*Pistil.*—1.0 cm.

*Stigma.*—RHS 71A (red-purple).

*Style.*—RHS 71A (red-purple).

*Petal size.*—1.8–1.2 cm (l×w).

*Petal margin.*—Sinuate.

*Petal apex shape.*—Retuse.

*Petal texture.*—Smooth and soft.

*Petal color.*—Upper surface RHS N78A (purple) with RHS 13B (yellow); base of petal inner surface RHS N78A (purple); outer surface RHS 13B (yellow).

*Produces seed.*—No.

*Habit.*—The flowers bloom during midmorning and close at night. Each flower blooms only once and are produced throughout the growing season. The plants produce flowers regardless of day length; the plants are day neutral. Plants can have 40 to 50 open flowers at one time and have no fragrance.

*Hardiness.*—Plant is heat tolerant; thrives in heat and humidity; plant is not cold tolerant or below 7° C.

Disease and Insect Resistance

No unusual susceptibility to diseases or insects have been observed.

Comparison with Other Known Varieties

'Kakegawa CY4' is most similar to the variety 'Duet Rose' (not patented). Both plants have similar foliage, a prostrate habit and bi-color flowers, however the rose with yellow petal margin pattern in 'Kakegawa CY4' is more uniform from plant to plant and more stable under different environmental conditions than with 'Duet Rose'.

I claim:

1. A new and distinct Portulaca plant as shown and described herein.

* * * * *

UNITED STATES PATENT AND TRADEMARK OFFICE
Certificate

Patent No. PP 16,152 P3 Patented: December 13, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Hiromi Matsukizono, Kagoshima Prefecture (JP).

Signed and Sealed this Fourth Day of December 2007.

WILLIAM R. DIXON, JR.
*Special Program Examiner*
Technology Center 1600